United States Patent
Adams et al.

(10) Patent No.: US 7,557,922 B2
(45) Date of Patent: Jul. 7, 2009

(54) DETECTION SYSTEM FOR USE IN A SORTING APPARATUS, A METHOD FOR DETERMINING DRIFT IN THE DETECTION SYSTEM AND A SORTING APPARATUS COMPRISING SUCH DETECTION SYSTEM

(75) Inventors: Dirk Adams, Tongeren (BE); Bert Peelaers, Herentals (BE); Bert Dirix, Genk (BE)

(73) Assignee: Visys NV, Halen (BE)

( * ) Notice: Subject to any disclaimer, the term of this patent is extended or adjusted under 35 U.S.C. 154(b) by 0 days.

(21) Appl. No.: 11/435,007

(22) Filed: May 16, 2006

(65) Prior Publication Data

US 2007/0030476 A1 Feb. 8, 2007

(30) Foreign Application Priority Data

May 17, 2005 (EP) .................................. 05447113

(51) Int. Cl.
*G01J 3/50* (2006.01)
*G01N 21/00* (2006.01)

(52) U.S. Cl. .................... 356/402; 356/446; 209/577
(58) Field of Classification Search .............. 356/237.2, 356/402, 425; 209/576, 577, 579, 580, 581
See application file for complete search history.

(56) References Cited

U.S. PATENT DOCUMENTS

| 3,545,610 | A | | 12/1970 | Kelly et al. |
| 5,216,485 | A | * | 6/1993 | Bird et al. .................... 356/394 |
| 5,220,617 | A | * | 6/1993 | Bird et al. .................... 382/149 |
| 5,847,823 | A | * | 12/1998 | Imaino et al. ............. 356/243.1 |
| 5,867,261 | A | * | 2/1999 | Imaino et al. ............. 356/237.2 |
| 5,917,589 | A | * | 6/1999 | Imaino et al. ............. 356/237.2 |
| 5,933,230 | A | * | 8/1999 | Imaino et al. ............. 356/237.2 |
| 5,969,370 | A | * | 10/1999 | Imaino et al. .......... 250/559.06 |
| 6,100,971 | A | * | 8/2000 | Imaino et al. ............. 356/237.2 |
| 6,117,620 | A | * | 9/2000 | Imaino et al. ............... 430/320 |
| 6,509,537 | B1 | | 1/2003 | Krieg et al. |
| 6,624,884 | B1 | * | 9/2003 | Imaino et al. ............. 356/237.2 |
| 6,704,435 | B1 | * | 3/2004 | Imaino et al. ............... 382/108 |

FOREIGN PATENT DOCUMENTS

| EP | 0 952 895 B1 | 7/1998 |
| EP | 0 957 353 A2 | 11/1999 |
| WO | WO 2004/105967 A1 | 12/2004 |

* cited by examiner

*Primary Examiner*—F. L Evans
(74) *Attorney, Agent, or Firm*—Merchant & Gould P.C.

(57) ABSTRACT

The present invention is related to a detection system for inspecting a continuous stream of products comprising means for determining the detection system induced variations in its output signal. The detection system comprises a reference element and an intermediate optical element, means for scanning a light beam over the product stream and, via the intermediate optical element, over the reference element and means for converting the light beams re-emitted by the product stream and by the reference element into an electrical signal. The intermediate optical element is positioned such that the light beam successively scans the product stream and at least one region of the reference element, in whatever order. Such detection system and method are of particular use in an apparatus for sorting products, where it is used to inspect products provided to the detection system in a continuous stream.

17 Claims, 8 Drawing Sheets

DETECTION SYSTEM FOR USE IN A SORTING APPARATUS, A METHOD FOR DETERMINING DRIFT IN THE DETECTION SYSTEM AND A SORTING APPARATUS COMPRISING SUCH DETECTION SYSTEM

PRIORITY

This application claims priority to European application EP05447113 filed on May 17, 2005.

FIELD OF THE INVENTION

The present invention relates to a method and system for detecting the optical properties of products, which are provided to the system in a continuous stream. In particular the present invention relates to a method for determining the variation in the output signal of the detection system.

STATE OF THE ART

A sorting apparatus for granular products is disclosed in European patent EP0952895. This sorting apparatus comprises a detection system, a removal system and a transport device having a sloped distribution surface. This transport device guides the products towards the detection and removal system such that products are analysed and selected while moving in a vertical downward direction. The individual products are sorted with the help of the detection system detecting and analysing one or more predetermined characteristics of each product. Typically optical parameters are being detected, such as colour, shape etc. When these characteristics are outside a predetermined acceptance range, i.e. the product doesn't meet the desired quality level, this product will be removed from the product stream. The detection system will inform the removal system about whether a specific product is accepted or rejected. After inspecting each individual product the detection system will provide the removal system with information about the position and speed of the rejected product needed to locate this product such that when this rejected product passes in front of the removal system, it can be removed from the product stream.

The configuration of such detection system is illustrated by patent document U.S. Pat. No. 6,509,537. This sorting apparatus comprises a conveyor for transporting a stream of solid particles and a device for detecting and differentiating between the quality and/or the colour of the individual solid particles. The detection system comprises a laser beam, which is redirected towards the solid particles via a polygon wheel. Due to the rotation of the polygonal wheel the mirroring end surfaces of the wheel will azimuthally guide the laser beam in a temporal saw-tooth movement. The moving laser beam is then directed towards the stream of solid particles to provide a linear laser beam scan thereof. The laser beam, which is re-emitted by the solid particles in a divergent way, is redirected via the mirroring end surfaces of the wheel towards photoelectrical devices converting the optical signal into an electrical output signal. This output signal can then be further handled by analogue electrical circuitry or converted into a digital signal for digital processing and data manipulation.

If identical products were being analysed by such a detection system at different moments in time, one would expect an identical output signal to be generated by the detection system. The problem arises if, due to any variation or drift with this detection system, a variation in the electrical output signal occurs which is not caused by the properties of the analysed products. Consequently, an incorrect assessment of the product quality could be made resulting in acceptable products being rejected or unwanted products to be accepted. Such variation in the output signal can have multiple causes, e.g. fluctuation of the laser beam power, a change of the optical properties of the beam redirecting elements over time or a fluctuation in the efficiency with which the optical signal is converted into an electrical output signal. Another variation or offset on the electrical output signal created by the detection system is the dark current of the photoelectrical devices.

Prior solutions exist to determine, at least in a qualitative way, such product-independent variations of the electrical output signal. In patent application EP0957353 a reference member is available which is being measured at regular time intervals. It is assumed that the optical properties of this reference member remain constant over time. The electrical output signal obtained on such reference member is being compared with a preliminary stored reference signal. The deviation between both signals is used to correct the output signal obtained when measuring products. As this reference member is to be positioned in the optical path between the light projecting device and the products, e.g. by placing the reference member along the product stream, thereby requiring a complex handling mechanism, the detection and analysis of the products will be interrupted during every reference measurement. Hence, such compensation method cannot be used when analysing a continuous stream of products. In the latter case one could guide this stream of products in parallel with a fixed reference device, e.g. a background surface such as a rotatable drum positioned behind the product stream. The incident laser beam is re-emitted by the products but also by this background surface, both re-emitted optical signals follow the same optical path towards to photoelectrical devices. The electrical output signal corresponding to the background surface is used as reference signal. As the colour of this reference device corresponds to the colour of acceptable products, a continuous reference signal is obtained falling within the acceptance range for the given product. The signals of the individual products are then compared with this reference signal such that in case of an unacceptable deviation between both signals the corresponding product will be rejected. Although this method doesn't suffer from the shortcomings of EP0957353 it doesn't provide an optical signal into the detection system, which is constant over a considerable period of time. The background surface is typically made from materials which are susceptible to sunlight, furthermore it may get partially or completely covered with residues, originating for example from the product stream, such that its colour and/or light re-emitting properties will change as function of time resulting in a variation of the electrical reference signal which is not caused by the detection system. Also this method requires the product stream to be interrupted to allow cleaning of this background surface.

In U.S. Pat. No. 3,545,610 a white standard is available, which is placed in the scanning path just to one side of the limit of the belt scan. The purpose of this is to provide a standard or reference level to stabilize the output from the light detector. The set-up of U.S. Pat. No. 3,545,610 suffers from the same deficiencies as the set-up of EP0957353. The white standard may get partially or completely covered with residues, originating for example from the product stream, such that its colour and/or light re-emitting properties will change as function of time resulting in a variation of the electrical reference signal which is not caused by the detection system. Also, this method requires the product stream to be interrupted to allow cleaning of this background surface.

There is need for a correction method and a device for determining a variation in the electrical output signal of a detection system while detecting a stream of products, this variation being induced by the detection system itself. The device must be capable of generating an optical signal into the detection system, which optical signal is constant over a considerable period of time. Moreover, the electrical reference signal must be obtainable without interrupting the detection of the stream of the products.

AIMS OF THE INVENTION

The present invention aims to provide a method for determining drift in the output signal of a detection system for a sorting apparatus. In a second aspect it aims to provide a detection system wherein the method is applied. In a further aspect the invention aims to provide a sorting apparatus comprising such detection system.

SUMMARY OF THE INVENTION

In order to overcome the above problems the present invention discloses in one embodiment a detection system for in-line inspection of a stream of products, the detection system comprising a reference element, means for scanning a light beam over the product stream and, via an intermediate optical element, over the reference element and means for converting the light beams re-emitted by the product stream and by the reference element into an electrical signal. The reference element and the intermediate optical element are positioned such that the light beam successively scans the product stream and, via this intermediate optical element, at least one region of the reference element, in whatever order. The reference element and the scanning means are positioned at the same side of and at a certain distance from the product stream. The intermediate optical element can be a mirror redirecting the scanning light beam towards the reference element. The total optical path length of each light beam received by the conversion means needs to be substantially the same, whether being re-emitted by the product stream or by the reference element. Alternatively this requirement can be achieved when the intermediate optical element is a focusing means, thereby making it possible to have a different path length for each light beam while still being able to focus both the image of the product as well as the image of the reference element onto the conversion means. Focusing the beam towards the conversion means is necessary to measure certain aspects of the beam itself by means of special diaphragms, as is well known in the art.

One embodiment of the present invention discloses a detection system according to any of the other embodiments contained in closed environment configured to only allow passage of the light beam for scanning the product stream.

Another embodiment of the present invention discloses the reference element in a detection system according to any of the other embodiments comprising at least two sections which are scanned by the light beam. These at least two sections differ in optical properties, for example one section can be coloured black while other sections are coloured differently.

Another embodiment of the present invention discloses the reference element in a detection system according to any of the other embodiments wherein the optical properties of the reference element can be adjusted in view of the products to be analysed.

A preferred embodiment of the present invention discloses a detection system according to any of the other embodiments comprising a scanning means containing at least one optical source for emitting a light beam, a first mirror being positioned to redirect the emitted light beam through an opening in a second mirror towards a rotatable polygon wheel having reflecting end surfaces, the second mirror being positioned to redirect a light beam reflected by the polygon wheel towards the second mirror to the conversion means, a third mirror being positioned to reflect a light beam from the polygon wheel to the reference element and vice versa, and said conversion means comprises at least one photomultiplier.

Another embodiment of the present invention discloses a sorting apparatus comprising a detection system according to any of the foregoing embodiments, and a supply system for transporting and guiding the product stream towards the detection system. The sorting apparatus is preferably used for in-line sorting a continuous stream of products.

In another aspect the invention discloses a method for correcting for the drift in a detection system as previously described when in use, comprising the steps of:
generating at least one reference signal at the output of said conversion means by scanning a reference element via said intermediate optical element,
generating at least one product signal at the output of said conversion means by scanning at least one product, and
said reference element and said at least one product being scanned successively, such that during one scan movement said at least one reference signal and said at least one product signal are successively generated.

SHORT DESCRIPTION OF THE DRAWINGS

For the purpose of teaching the invention schematic viewings and cross-sections of a detection system according to various embodiments of the invention are given. These drawings are not to scale. Like numerals are given to like elements in each drawing.

DETAILED DESCRIPTION OF THE INVENTION

The present invention discloses a detecting system for inspecting products which are provided to the detection system in a continuous stream. The detection system comprises means for determining the variation in the output signal of the detection system, in particular the variation caused by the detection system itself such as drift or dark current.

Figure 1:
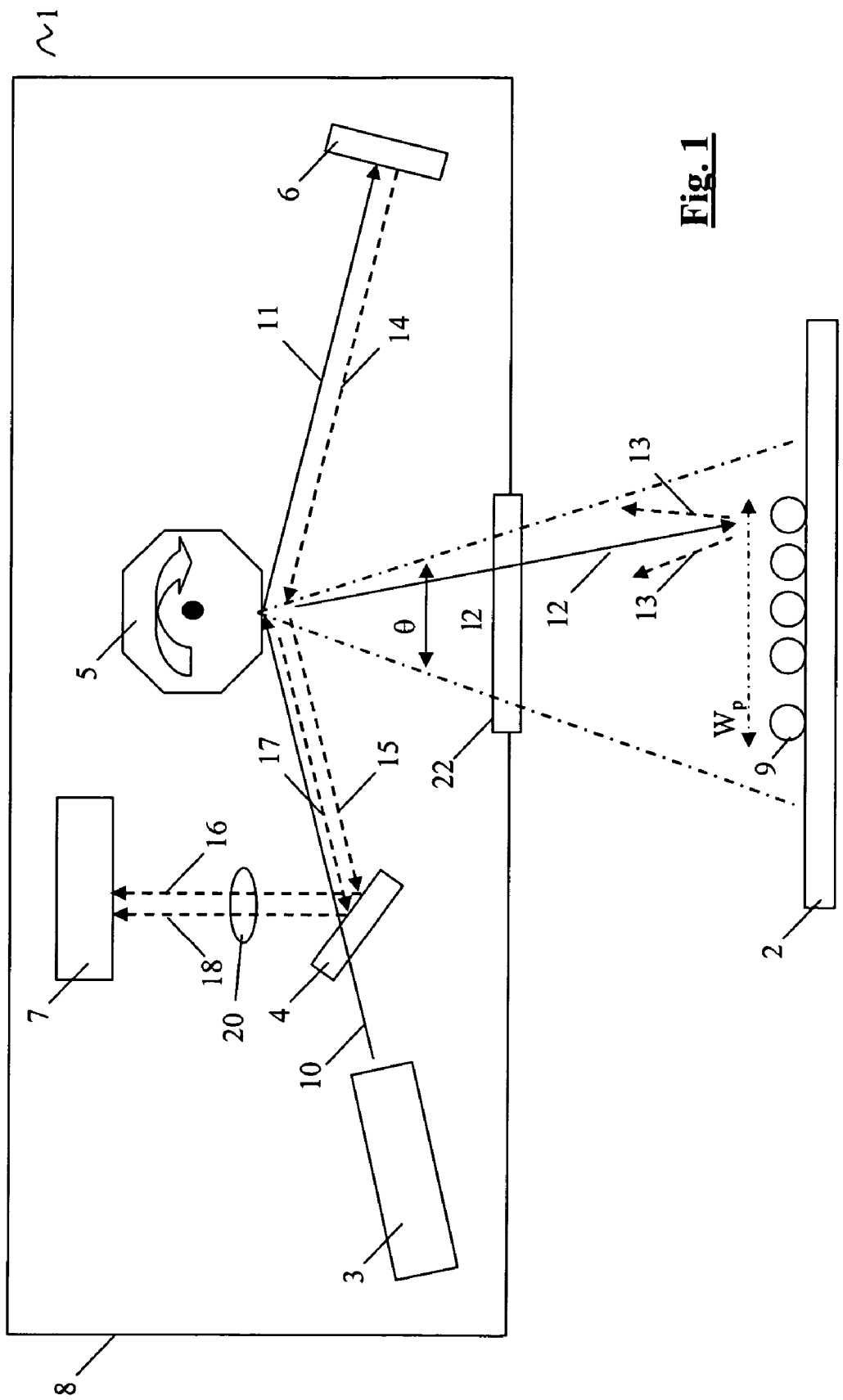
FIG. 1 represents a schematic view of a detection system according to an embodiment of the invention.

FIG. 1 illustrates a first embodiment of the invention showing a detection system (1) and a supply system (2) for transporting products (9), typically in a continuous stream, along the detection system for inspection. The detection system comprises at least one light source (3) for generating a light beam (10) having a predetermined wavelength which is chosen in function of the product to be analysed as is known in the art. This light source can be a laser generating a laser beam. This light beam (10) will be guided (12) via an optical system (4, 5) over the product stream such that the light beam scans over an angular range θ at least comprising the product stream. If the scanning is done in a linear manner, all products within the width $w_p$ of the product stream are being irradiated by the light beam (12) going back and forth. The irradiated product will re-emit light beams (13) characteristic for the product, typically in a divergent way. This re-emitted light (13) is guided (15, 16) via an optical system (4, 5, 20) to a conversion means (7) which can be a photoelectrical device such as a photodiode or photomultiplier. The focusing means (20) is configured such that the re-emitted light is focused towards the conversion means (7). The light beam (16) incident on the photoelectrical device is converted by this device in an electrical output signal (p) characteristic for the product from which this light beam (16) stems. This signal is processed to determine whether or not this product passes the selection requirements. The value of this output signal (p) will inter alia be function of the properties of the inspected product and of any variations induced by the detection system.

The detection system shown in FIG. 1 further comprises a reference element (6). The light beam (10) is also guided (11) by the optical system (4, 5) over this reference element (6) thereby generating a reflected light beam (14), which is redirected (17, 18) by the optical system (4, 5, 20) to the photoelectrical device (7). Again the focusing means (20) is used to focus the image towards the conversion means (7). Here the incident light beam (18) is converted in a reference signal (r). The value of this reference signal will be prone to any variations induced by the detection system itself. It will vary with the power of the light source (3) or with a change in conversion efficiency of the photoelectrical device (7). A dark current present in this photoelectrical device (7) will offset the reference signal (r). Typically a first measurement of the reference signal (r) is done when the detection system is accepted and put into use. The value of this first measurement is stored. During the lifetime of the detection system (1) the reference signal (r) is measured at regular time intervals yielding a sequence of measurement data, which are also stored. By comparing the measured values of the reference signal (r) one can determine the variation in the output of the photoelectrical device (7) caused by the components (3, 4, 5, 7) of the detection system itself. When the detection system is used to inspect products; this variation can then be taken into account to compensate and correct the electrical output signal (p) corresponding to an inspected product such that its value is a true representation of the physical properties of this product.

Figure 2:
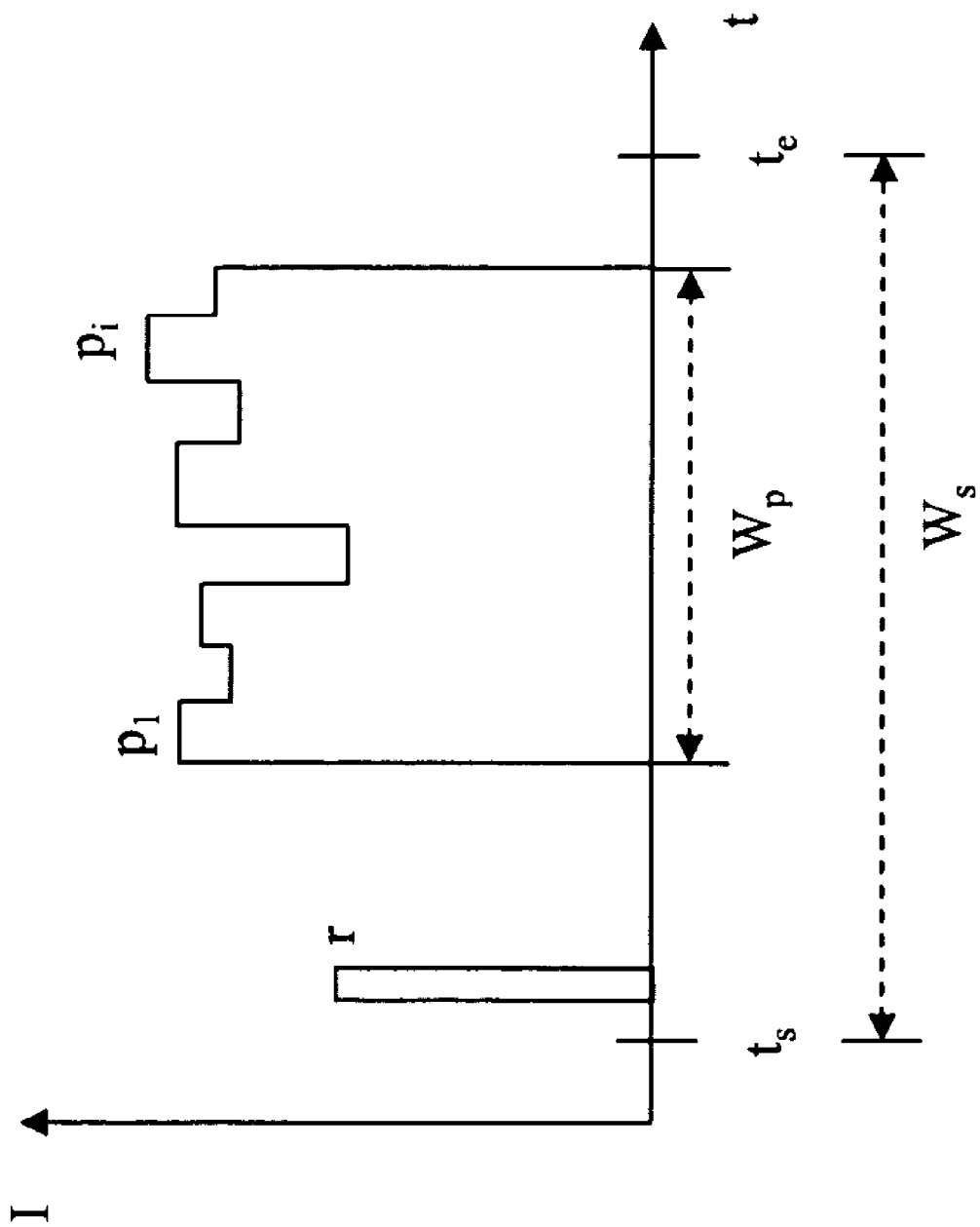
FIG. 2 represents a typical electrical output signal I of a detection system according to an embodiment of the invention obtained during one scan θ.

As shown in FIG. 1 the position of the reference element (6) is carefully chosen such that it can be scanned by the same light beam (10) scanning the stream of products (9) without influencing the light beams to (12) and from (13) these products (9). In the embodiment of FIG. 1 the light beam (10) is first guided (12) over the product stream and then over the reference element (6). However, the products (9) and the reference element (6) can be scanned in any succession, the sequence depending on the relative position of the products (9) and of the reference element (6) and on the scanning direction of the light beam (10). As the reference element (6) and the product stream are scanned one after another, the corresponding re-emitted or reflected light beams (13, 14) will result in successive electrical signals (p,r) at the output of the photoelectrical device (7) as illustrated in FIG. 2, showing the electrical signal I of one scan of the light beam (10). Such signals can be obtained by the detection system (1) illustrated by FIG. 1. At the start $t_s$ of the scan first the reference element (6) is scanned resulting in a reference signal (r) outputted by the photoelectrical device (7). Thereafter the product stream is scanned resulting in a series of product signals ($p_i$) outputted by the photoelectrical device (7), each product signal ($p_i$) corresponding to an individually inspected product. The length of the envelope of the product signals ($p_i$) depends on the width $w_p$ of the product stream while the period $t_s$-$t_e$ corresponds to the width $w_s$ of the scan. As the reference element (6) and the products (9) are consecutively scanned during one scan, the corresponding electrical signals at the output of the photoelectrical device (7) will also appear consecutively in the scan signal I.

To enable such successive scanning of the products (9) and of the reference element (6), the reference element (6) and the scanning means (3, 4, 5) of a detection system (1) are preferably placed at the same side of the product stream, but at a predetermined distance there from. The distance between the supply system (2) carrying the products (9) on the one hand and the detection system (1) comprising the reference element (6) and the scanning means (3, 4, 5) on the other hand can be chosen, inter alia as function of the product (9) to be inspected, the wavelength of the light beam (10), geometrical constraints of the sorting apparatus comprising the detection system etc. Depending on the direction in which the products (9) are moving during inspection, e.g. in a horizontal or vertical direction, the detection system can be placed at an elevated or inclined position with respect to the stream of products (9) or additional optical means can be provided to have the light beam (10) scanning the products (9) impinging thereon at the desired angle of incidence.

Preferably the detection system (1) is placed in a closed environment (8). As the propagation (12, 13, 15, 16, 11, 14, 17, 18) of the light beam (10) in the detection system is affected by any contamination of the optical components (3, 4, 5, 6, 7, 20) of the detection system (1) or by any residues present within the optical path of the light beam (10), measures need to be taken to protect these sensitive optical components (3, 4, 5, 6, 7, 20) of the detection system (1) from the, sometimes harsh, production environment wherein the products (9) are handled. A box (8) can be placed over the entire detection system (1) shielding this system (1) from the production environment. However this box (8) must be configured to still allow passage (12) of the light beam (10) for scanning the products (9). As illustrated in FIG. 1, an opening (22) must be made in the sidewall of the box (12) through which the light beam (10) can go to (12) and from (13) the product stream for scanning thereof. Preferably this box (8) is adapted to form a closed and sealed environment which is put at a given pressure. As the inner side of the box (8) is at a pressure higher than the pressure of the production environment, the flow of contaminants or residues into the box (8) is significantly reduced. In this case no effective opening is formed in the sidewall of the box (8), but a region (22) in a material transparent to the light beam (10) is provided while maintaining the pressure inside.

The light generated by the light source (3) will diverge during its propagation. Only a portion of the generated light will finally be received by the conversion means (7). However, as much light as possible should be received by the conversion means (7) to improve the accuracy of the product analysis. Preferably the light rays (16,18) received at the conversion means (7) coming from the reference element (6)

and from the products (9) have substantially the same intensity. An advantage thereof is that the conversion means (7) can be calibrated in substantially the same intensity range and/or intensity level as the range or level in which the conversion means (7) will operate when analysing the stream of products (9).

Figure 4:
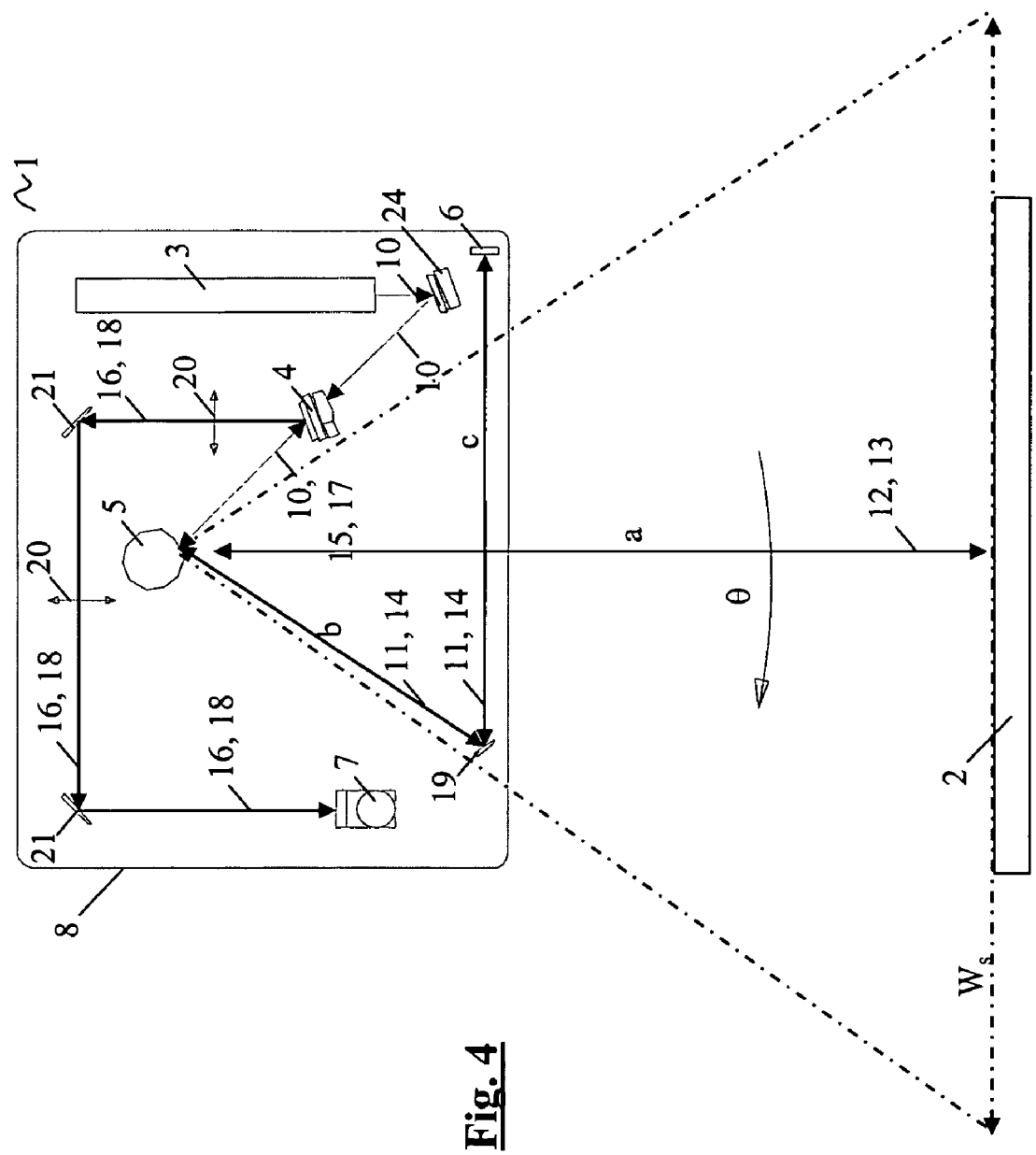
FIG. 4 represents a schematic view of a detection system according to a preferred embodiment of the invention.

Preferably the reference element (6) is positioned such that the light beams (12-13-15-16, 11-14-17-18) received by the conversion means (7) will have substantially the same total optical path length (FIG. 4: a=b+c). FIG. 4 shows the optical paths followed by the light beams. A first optical path goes from the light source (3) via the mirrors (4,24) and the polygon wheel (5) to the product (9) and back via the polygon wheel (5) and the mirror (4) to the conversions means (7) while the light will be focused by the focusing lenses (20). The light beam following this first optical path will result in a product signal (p). A second optical path goes from the light source (3) via the mirrors (4,24), the polygon wheel (5) and mirror (19) to the reference element (6) and back via the mirror (19), the polygon wheel (5) and the mirror (4) to the conversions means (7) while again being focused by the focusing lenses (20). The light beam following this second optical path will result in a reference signal (r). Both optical paths coincide to a large extent, as the light beam resulting in a reference signal (r) should be handled by as much as possible components in common with the light beam resulting in a product signal (p). This way the correction of the product signal (p) by the reference signal (r) will be more accurate. For the detection system (1) shown in FIG. 4 the first and second optical path will only differ in the optical length of the section (a) and section (b,c) respectively. In this configuration it is sufficient if the reference element is positioned such that the section (b+c) has the same optical length as the section (a).

As shown in FIG. 4, the light beam (11) guided by the polygon wheel (5) will not directly impinge on the reference element (6), but will reach this reference element (6) via an intermediate optical element (19). Thanks to this intermediate optical element (19), the geometrical distance between the polygon wheel (5) and the reference element (6) can be considerably reduced as there is no need to e.g. position the reference element (6) in the vicinity of the product (9) stream. If a mirror is used as intermediate optical element (19) as illustrated in FIG. 4, the light path between the polygon wheel (5) and the reference element (6) is folded such that, the geometrical distance between the polygon wheel (5) and the reference element (6) is substantially less than the distance between the polygon wheel (5) and the products (9) being analysed, while the section (b+c) will have substantially the same optical length as the section (a).

Another advantage of the detection system illustrated by FIG. 4 is that a compact detection system (1) is obtained containing the means for generating a light beam (10) towards the products (9) and towards the reference element (6), the means for receiving the light re-emitted (16) from these products (9) and for receiving the light (18) reflected by the reference element (6), means to focus (20), and the means (7) for converting the received light (16,18) into an electrical signal. Hence, the elements of the detection system (1) easily can be contained within a box (8) shielding these elements at least from the product stream or from the environment in which the product analysis takes places. Neither the detection system (1) nor the shielding box (8) needs to be placed in close vicinity of the products (9). Thanks to the compactness of the detection system (1) the shielding box (8) can be of a simple design, e.g. a rectangular box or any cuboid such as a cubic.

Figure 5:
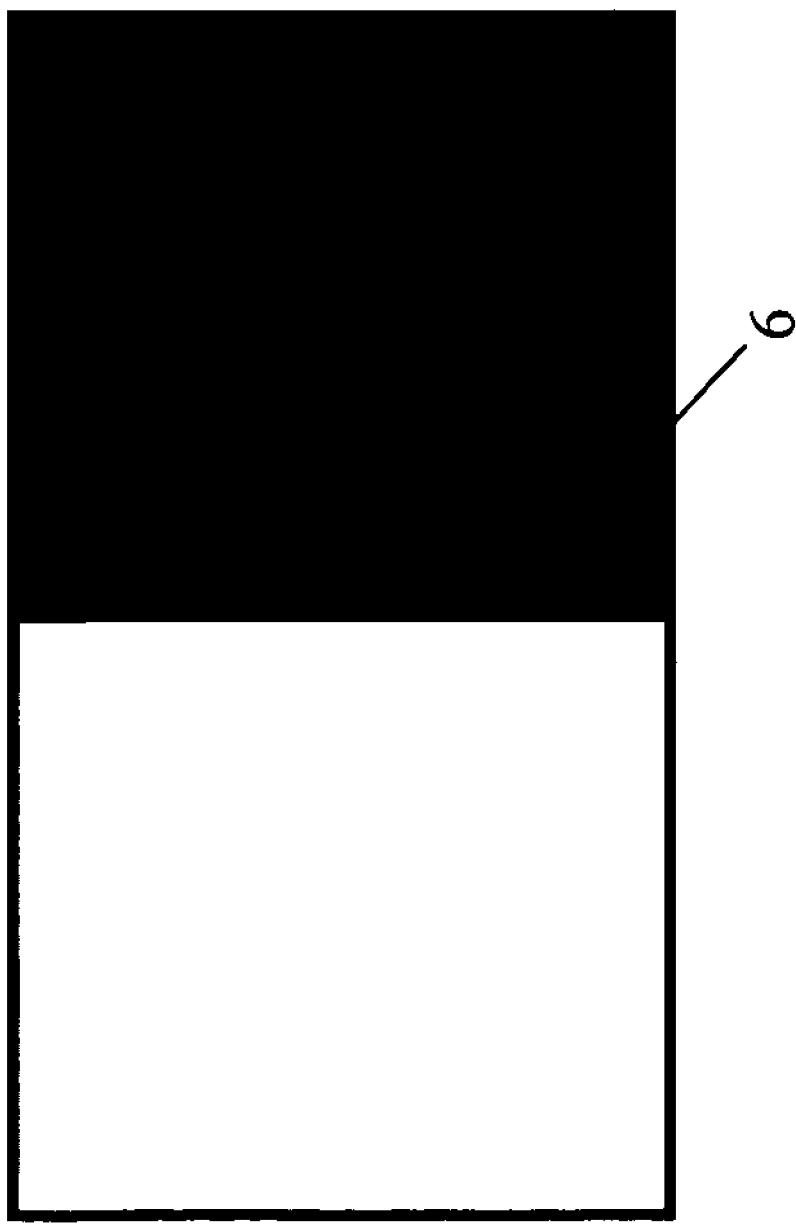
FIG. 5 represents a schematic view of a two-sectioned reference element according to an embodiment of the invention.

The physical properties, e.g. its colour, of the reference element (6) are selected in function of the products (9) to be inspected, the frequency and/or signal range in which the photoelectric device (9) operates and the type of system-induced variation one intends to measure. If for example the dark current of the photoelectric device (7) is to be assessed a black coloured reference element (6) is used. The thus obtained reference signal (r) corresponds to non-optical signal (18) at the input of the photoelectrical device (7) and hence only the electrical signal generated by the photoelectrical device (7) itself is detected. Instead of using reference elements (6) with different physical properties one can use a single reference element (6) comprising various sections, each section having different physical properties. A multi-sectioned reference element (6) has the advantage of creating multiple reference signals ($r_i$) with a single element thereby avoiding the replacement of the reference element (6). If, as discussed in another embodiment of the invention, the detection system (1) is placed in a sealed environment, replacing the reference element (1) e.g. because another type of product (9) is to be inspected, would be time-consuming and labour-intensive. Each of the different sections can be selected e.g. for use with a specific type of product (9) or for determining a different type of system-induced variation. FIG. 5 shows a passive reference element (6) containing two sections: a white coloured section (left) and a black coloured section (right).

Figure 6A:
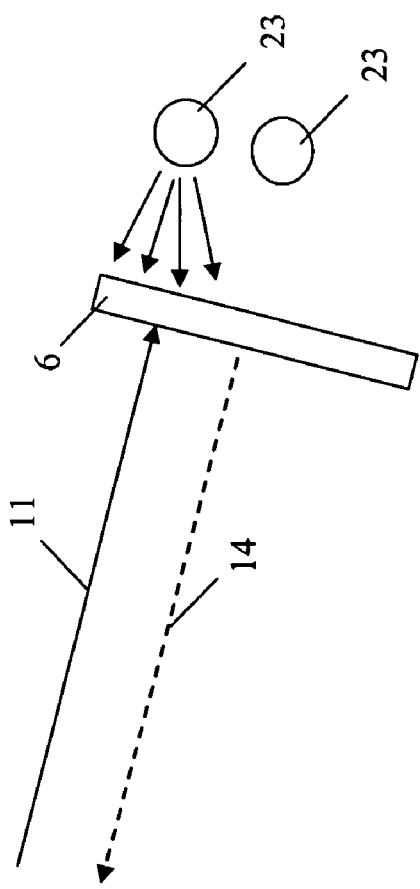
FIGS. 6a and 6b represent a schematic view of an active reference element according to another embodiment of the invention.
Figure 6B:
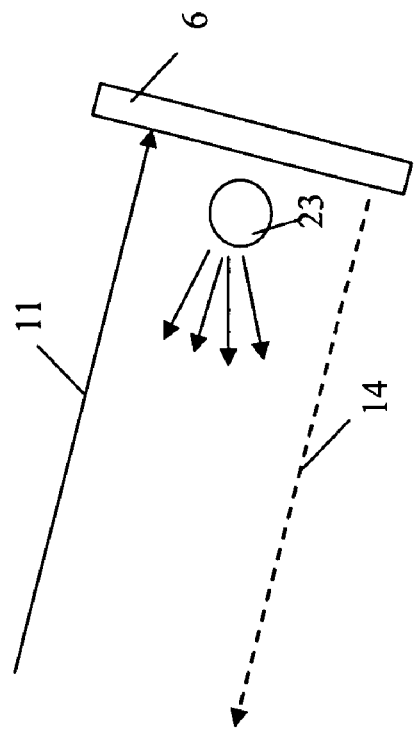

The optical properties of the reference element (6) can be varied by providing a multi-sectioned reference element, each section having given optical properties, or by varying the optical properties of the reference element (6) when the detection system (1) is in use. Such active reference element (6) then comprises means (23) for adjusting the optical properties thereof. The reference element (6) can be constructed as a transparent or diffusing screen on one side thereof the light beam (11) impinges while on the other side light emitting diodes (LED) are provided to illuminate the transparent screen. Depending on the illumination conditions, the transparent or diffusing screen will have a different outlook, i.e. a selected colour with a selected intensity. The intensity of the light emitted by a LED can be varied by varying the current through the LED. The wavelength of the emitted light can be varied by selecting the appropriate LED, FIG. 6 illustrates such an active reference element containing two LED's (23) e.g. one can select between a green LED (top) and red LED to illuminate the transparent screen with the selected intensity. In the embodiment illustrated in FIG. 6a only the top LED is illuminating the reference element (6). Alternatively, as depicted in FIG. 6b, the LEDs can be positioned in front of the reference element (6) such that the returning light (14) will be the sum of the reflected light due to the light (11) impinging on the reference background and the light emitted by the LED.

Figure 3:
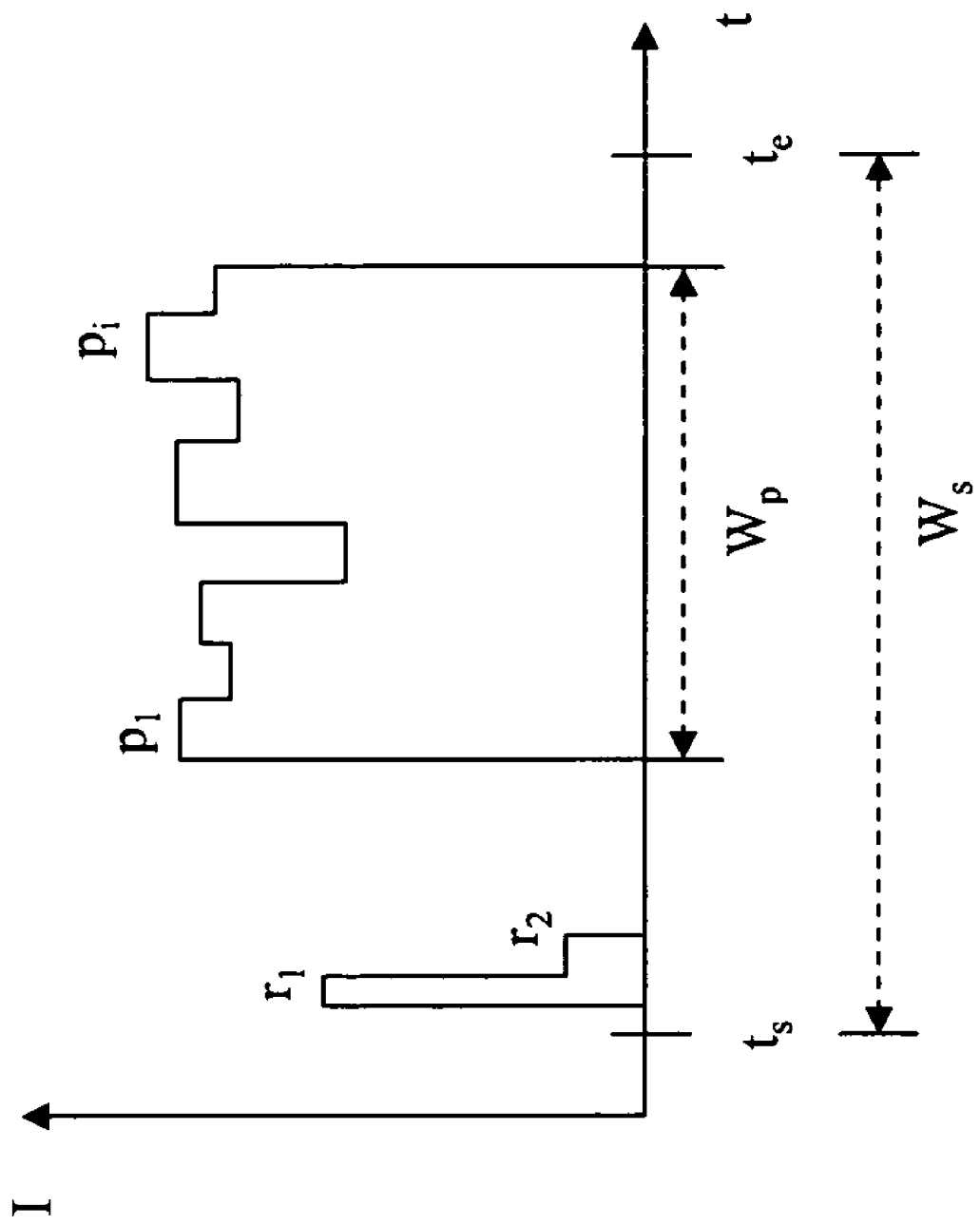
FIG. 3 represents a typical electrical output signal I of a detection system according to an another embodiment of the invention obtained during one scan θ.

FIG. 3 shows the electrical signal I of one scan of the light beam (10) in case a reference element (6) containing two sections is used, a first section having a predetermined colour different from black and a second section being black coloured. At the start $t_s$ of the scan first the reference element (6) is scanned resulting in two reference signals ($r_i$) outputted by the photoelectrical device (7). The first reference signal ($r_1$) is indicative of the colour of the first region and of the variations within the detection system (1), while the second reference signal ($r_2$) is indicative of the dark current of the photoelectrical device (7) as discussed above. Thereafter the product stream is scanned resulting in a series of product signals ($p_i$) outputted by the photoelectrical device (7).

FIG. 4 shows a preferred embodiment of the invention. The laser (3) generates a laser beam (10), which is reflected by a first mirror (24) through an opening located at the centre of a second mirror (4) towards a rotatable polygon wheel (5) having reflecting end surfaces. More than one laser (3) can be present, each laser having a different wavelength. This can be useful if e.g. a spectral analysis of the products (9) is to be performed. As disclosed in patent document U.S. Pat. No. 6,509,537 this polygon wheel (5) will, when rotating, guide the laser beam (10) in a temporal saw-tooth movement θ over the reference element (6) and over the product (9) stream. The laser beam (10) will be guided (12) over the products (9) resulting in divergent re-emitted light beam (13) from the products (9) towards the polygon wheel (5). At an outer position of the scan θ a third mirror (19) is positioned to reflect the laser beam (10) from the polygon wheel (5) along the path (11) to the reference element (6) and from the reference element (6) along the path (14) to the polygon wheel (5). The second mirror (4) is positioned to reflect in its turn light reflected (15,17) by the polygon wheel (5) along the path (16,18) to the conversion means (7), e.g. a photomultiplier, while being focused by the focusing means (20) towards the conversion means (7). Additional optical elements can be positioned in the optical path between the second mirror (4) and the conversion means (7), such as diaphragms (not shown) and mirrors (21).

Figure 7:
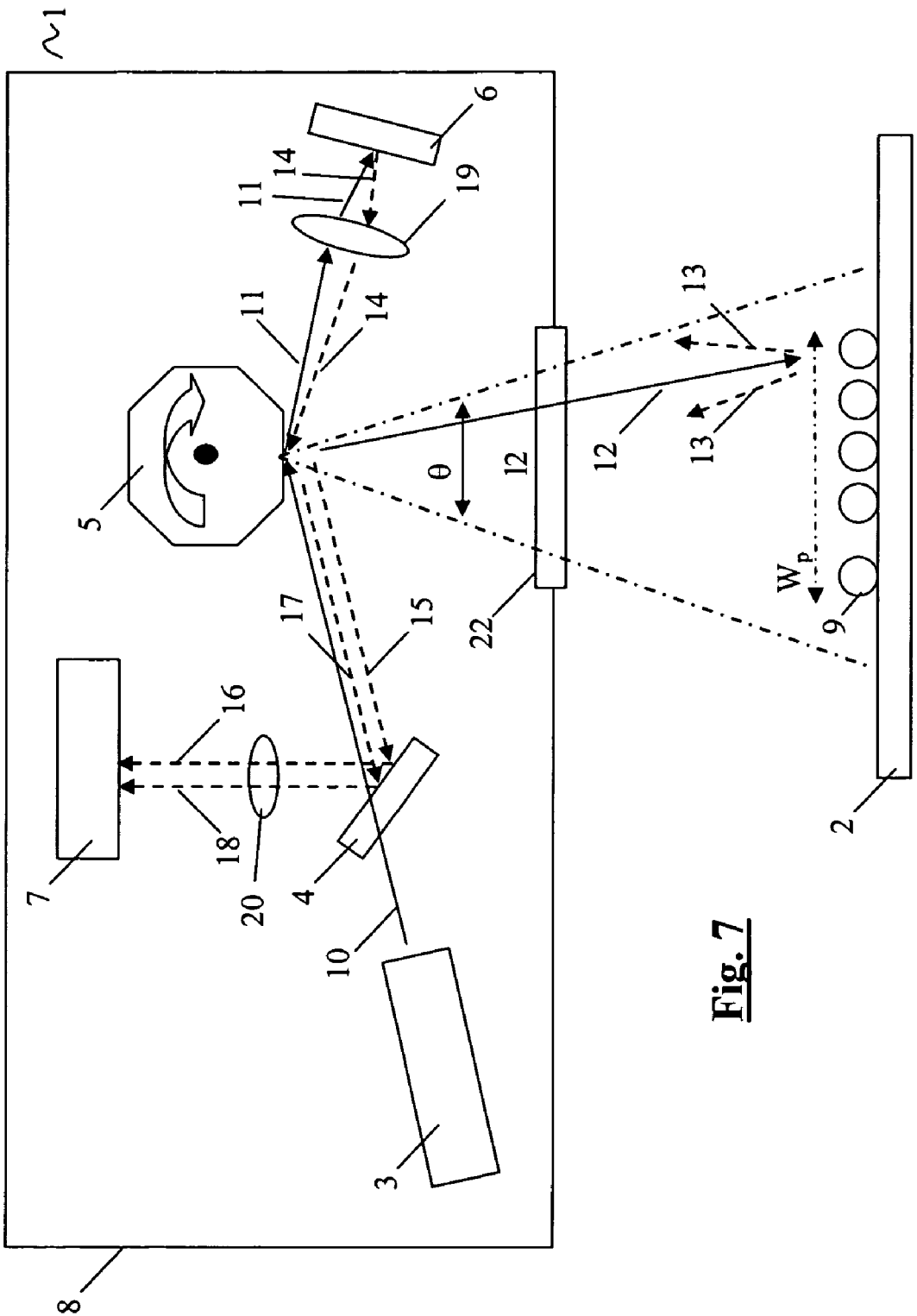
FIG. 7 represents a schematic view of a detection system according to another embodiment of the invention.

FIG. 7 illustrates another embodiment of the invention showing a detection system (1) and a supply system (2) for transporting products (9), typically in a continuous stream, along the detection system for inspection. The detection system comprises at least one light source (3) for generating a light beam (10) having a predetermined wavelength which is chosen in function of the product to be analyzed as is known in the art. This light source can be a laser generating a laser beam. This light beam (10) will be guided (12) via an optical system (4, 5) over the product stream such that the light beam scans over an angular range θ at least comprising the product stream. If the scanning is done in a linear manner, all products within the width $w_p$ of the product stream are being irradiated by the light beam (12) going back and forth. The irradiated product will re-emit light beams (13) characteristic for the product, typically in a divergent way. This re-emitted light (13) is guided (15, 16) via an optical system (4, 5, 20) to a conversion means (7) which can be a photoelectrical device such as a photodiode or photomultiplier as discussed in the embodiments illustrated by FIG. 1.

The detection system shown in FIG. 7 further comprises a reference element (6) and an intermediate optical element (19). The light beam (10) is also guided (11) by the optical system (4,5) via an intermediate optical element (9) over this reference element (6) thereby generating a reflected light beam (14), which is redirected (17,18) by the optical system (4,5,20) to the photoelectrical device (7). In the embodiment illustrated by FIG. 7 the intermediate optical element (19) is a lens which together with focusing means (20) will focus the diverging light beam (14) re-emitted by the reference element (6) towards the conversion means (7). Thanks to this intermediate optical element (19), the geometrical distance between the polygon wheel (5) and the reference element (6) can be considerably reduced as there is no need to e.g. position the reference element (6) in the vicinity of the product (9) stream and compact detection system (1) is obtained.

Figure 8:
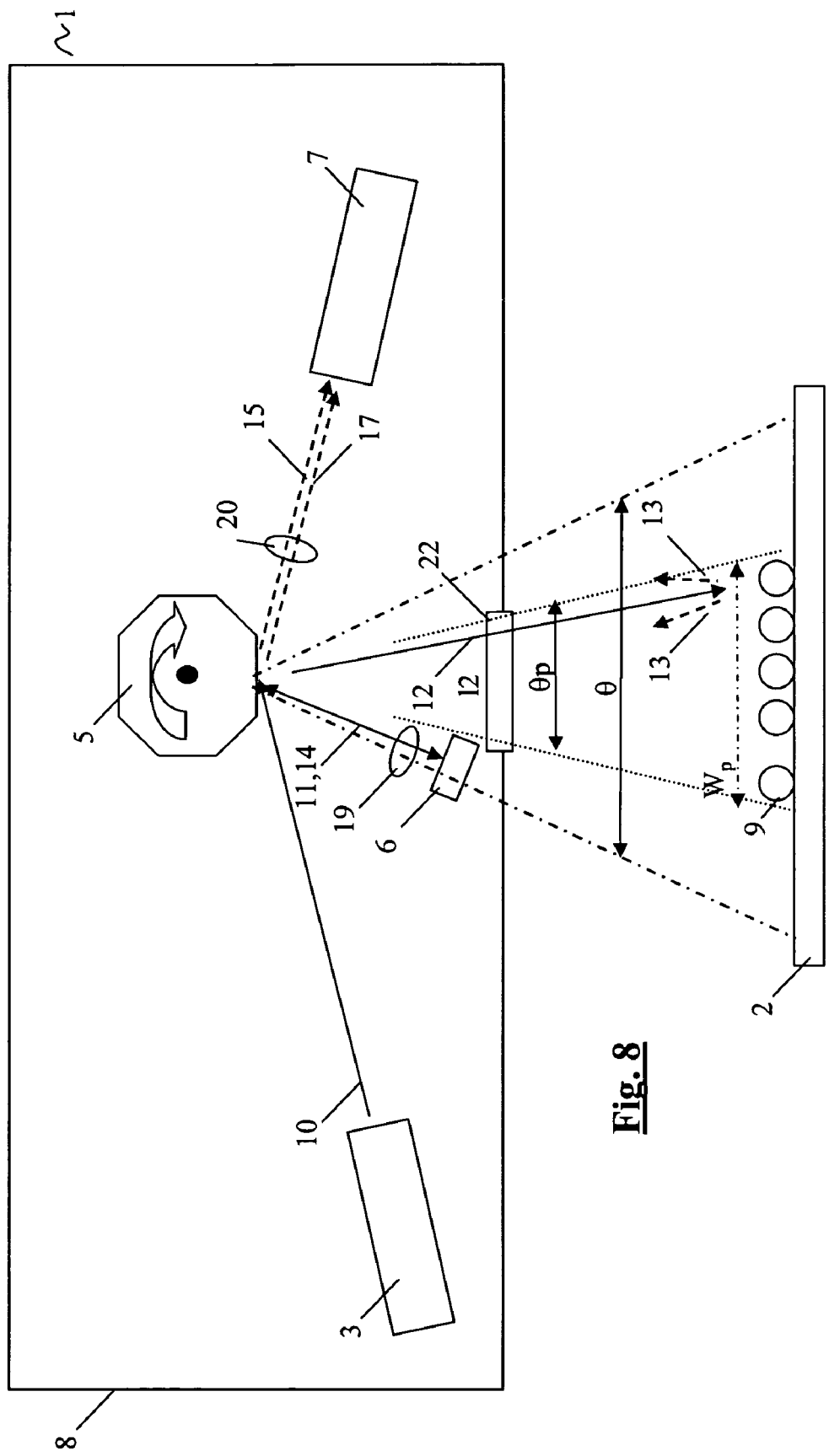
FIG. 8 represents a schematic view of a detection system according to another embodiment of the invention.

As the reference element (6) and the product (9) stream are scanned one after the other, the corresponding re-emitted or reflected light beams (13,14) will result in successive electrical signals (p,r) at the output of the photoelectrical device (7) as illustrated by FIG. 2 and discussed in the corresponding paragraph. In the embodiment of FIG. 7 the light beam (10) is first guided (12) over the product stream and then via the intermediate optical element (19) over the reference element (6). However, the products (9) and the reference element (6) can be scanned in any succession, the sequence depending on the relative position of the products (9) and of the intermediate element (19) and on the scanning direction of the light beam (10). An alternative configuration to the set-up illustrated by FIG. 7 is shown in FIG. 8. Here the light beam (10) is first guided, via the intermediate optical element (19) which is also a focusing lens, over the reference element (6) and then over the products (9).

The position of at least the intermediate element (19) is carefully chosen such that it can be scanned by the same light beam (10) scanning the stream of products (9) without influencing the light beams to (12) and from (13) these product (9). FIG. 4 illustrates that at least the intermediate optical element (19) must be placed within the angular range θ at least comprising the product stream. In the configuration illustrated by FIG. 4, the mirror (19) is positioned such that it is scanned (11) by the optical means (4,5). The reference element (6) itself is positioned outside of the angular scan range θ and is indirectly scanned via the scanning light beam which is redirected by the mirror (19) towards the reference element (6). FIG. 8 illustrates that the intermediate optical element (19) and the reference element (6) can be placed within the angular range θ at least comprising the product stream. However this angular range θ (between dash-dotted lines) is larger than the width $w_p$ of the product stream being irradiated by the light beam (12) going back and forth. FIG. 8 illustrates that the angle of product scan $\theta_p$ (between dotted lines) is determined by the dimensions of the opening (22) allowing passage (12) of the light beam (10) for scanning the products (9). In the region of the angular range θ not covered by the product scan range $\theta_p$ the intermediate optical element (19) and, in case of the intermediate optical element being a focusing lens, the reference element (6) are placed.

Such device and method are of particular use in an apparatus for sorting products, in particular for sorting granular products. Such sorting apparatus are known in the art. Typically a sorting apparatus comprises a transport and guiding system for providing the products to the detection system for inspection. Such transport and guiding system can comprise a conveyor, a vibrating table or shaker for transporting the products, a chute for guiding the free fall of the products towards the detection system. The sorting apparatus can further comprise a removal system for removing after inspection rejected products from the product stream. It is known in the art to use compressed air for removing products from the product stream. The removal system then comprises multiple nozzles for blowing compressed air towards the rejected products when passing in front of one of these nozzles. It is thus advantageous to equip such sorting apparatus with a detection system (1) according to any embodiments of the invention as the electrical output signal can be corrected taking into account the deviation of this output signal caused by the detection system itself. Consequently the number of incorrect decisions in the inspection process can be reduced and the yield of the on-line sorting process improved. A sorting apparatus can contain more than one detection system according to the invention. The detection systems (1) are then preferably positioned at opposite sides of the product stream, faced away from each other, such that a more complete inspection of the product stream is realised without interference between the individual detection systems (1).

It should be appreciated by those skilled in the art that various modifications and variations can be made in the present invention without departing from the scope and spirit of the invention. For example, any combination of focusing lenses, mirrors and other optical devices may be utilised to implement the focusing means (20) and the intermediate optical element (19). It is intended that the present invention include such modifications and variations as come within the scope of the appended claims and their equivalents.

The invention claimed is:

1. A detection system for inspecting a continuous stream of products, the product stream having a width, the system comprising:
   a reference element distant from the stream of products,
   an intermediate optical element for redirecting a light beam only to and from the reference element,
   means for scanning a light beam over the width of the product stream and over the reference element,
   means for converting the light beams re-emitted by said product stream and by said reference element into an electrical signal,
   the reference element and the intermediate optical element being positioned such that, when in use, the light beam successively scans the product stream and, via the intermediate optical element, at least one region of the reference element, wherein the intermediate optical element is outside the scan width of the product stream,
   the detection system being placed in a closed environment configured to only allow passage of the light beam to and from the product stream for scanning the product stream.

2. The detection system of claim 1, wherein said reference element and said scanning means are positioned at the same side at a predetermined distance to said product stream.

3. The detection system as in claim 1, wherein said intermediate optical element is a mirror being positioned to redirect said scanning light beam to and from said reference element.

4. The detection system as in claim 1, wherein the scanning means comprises: at least one light source for emitting a light beam, a first mirror positioned to redirect the emitted light beam through an opening in a second mirror towards a rotatable polygon wheel having reflecting end surfaces, said second mirror being positioned to redirect a light beam, reflected by said polygon wheel towards said second mirror, to said conversion means, and an intermediate optical element comprising a third mirror positioned to reflect a light beam from said polygon wheel to said reference element and vice versa; said conversion means comprising at least one photomultiplier.

5. The detection system as in claim 4, wherein said reference element and said third mirror are positioned such that the total optical path length of each light beam received by said conversion means is substantially the same.

6. The detection system as in claim 1, wherein said intermediate optical element is a focusing lens positioned to focus said scanning light beam towards said reference element.

7. The detection system as in claim 1, wherein said scanned at least one region comprises at least two sections, said at least two sections having different optical properties.

8. The detection system as in claim 7, wherein one of said at least two sections is coloured black.

9. The detection system as in claim 1, wherein said reference element further comprises means for adjusting the optical properties thereof.

10. A detection system for inspecting a continuous stream of products, the product stream having a width, the system comprising:
    at least one light source for emitting a light beam,
    a reference element distant from the stream of products,
    a first mirror being positioned to redirect the emitted light beam through an opening in a second mirror towards a rotatable polygon wheel having reflecting end surfaces,
    the second mirror being positioned to redirect a light beam reflected by the polygon wheel towards the second mirror to conversion means for converting the light beam into an electrical signal,
    a third mirror being positioned to reflect a light beam from the polygon wheel only to the reference element and vice versa, and
    the reference element and the third mirror being positioned such that, when in use, the light beam successively scans the product stream and, via the third mirror, at least one region of the reference element, and the detection system being placed in a closed environment configured to only allow passage of the light beam to and from the product stream for scanning the product stream.

11. A detection system for inspecting a continuous stream of products, the system comprising:
    at least one light source for emitting a light beam,
    a reference element distant from the stream of products,
    a first mirror being positioned to redirect the emitted light beam through an opening in a second mirror towards a rotatable polygon wheel having reflecting end surfaces,
    the second mirror being positioned to redirect a light beam reflected by the polygon wheel towards said second mirror to conversion means for converting the light beam into an electrical signal,
    a focus lens being positioned to focus a light beam only from the polygon wheel to the reference element and vice versa, and
    the reference element and the focusing lens being positioned such that, when in use, the light beam successively scans the product stream and, via the focusing lens, at least one region of the reference element, wherein the focusing lens is outside the scan width of the product stream, and the detection system being placed in a closed environment configured to only allow passage of the light beam to and from the product stream for scanning the product stream.

12. An apparatus for sorting a continuous product stream, comprising:
    a detection system comprising:
        a reference element distant from the product stream,
        an intermediate optical element for redirecting a light beam only to and from the reference element,
        means for scanning a light beam over the product stream and over the reference element,
        means for converting the light beams re-emitted by the product stream and by the reference element into an electrical signal, and
        the reference element and the intermediate optical element being positioned such that, when in use, the light beam successively scans the product stream and, via the intermediate optical element, at least one region of the reference element wherein the intermediate optical element is outside the scan width of the product stream,
        the detection system being placed in a closed environment configured to only allow passage of the light beam to and from the product stream for scanning the product stream, and
    a supply system for transporting and guiding the product stream in a continuous stream towards the detection system.

13. The sorting apparatus of claim 12, wherein said intermediate optical element is a mirror positioned to redirect the scanning light beam towards said reference element.

14. The sorting apparatus of claim 12, wherein said intermediate optical element is a focusing lens positioned to focus the light beam reflected by said reference element towards said conversion means.

15. A method for correcting for the drift in the optical performance of a detection system, when in use, the detection system comprising:
- a reference element distant from a product stream,
- an intermediate optical element for redirecting a light beam only to and from the reference element,
- means for scanning a light beam over the product stream and over the reference element,
- means for converting the light beams re-emitted by the product stream and by the reference element into an electrical signal, and
- the reference element and the intermediate optical element being positioned such that, when in use, the light beam successively scans the product stream and, via the intermediate optical element, at least one region of the reference element wherein the intermediate optical element is outside the scan width of the product stream, and
- the detection system being placed in a closed environment configured to only allow passage of the light beam to and from the product stream for scanning the product stream, the method comprising:
- generating at least one reference signal at the output of the conversion means by scanning a reference element only via said intermediate optical element, generating at least one product signal at the output of the conversion means by scanning at least one product, the reference element and the at least one product being scanned successively, such that during one scan movement the at least one reference signal and the at least one product signal are successively generated,
- determining the drift in the optical performance of the detection system from the reference signal, and
- correcting the product signal taking into account the determined drift.

16. A detection system for inspecting a continuous stream of products, the product stream having a width,
the system comprising:
- means for monitoring the optical performance of the detection system independent from the product stream;
- the monitoring means comprising:
  - a reference element spaced apart from the stream of products, the reference element being selected to monitor optical performance of the detection system;
  - an intermediate optical element for redirecting a light beam only to and from the reference element;
  - means for scanning a light beam over the width of the product stream and over the reference element;
  - means for converting the light beams re-emitted by the product stream and by the reference element into an electrical signal;
  - the reference element and the intermediate optical element being positioned such that, when in use, the light beam successively scans the product stream and, via the intermediate optical element, at least one region of the reference element, wherein the intermediate optical element is outside the scan width of the product stream; and
  - the detection system being placed in a closed environment configured to only allow passage of the light beam to and from the product stream for scanning the product stream.

17. The detection system of claim 16, wherein the reference element comprises a black colored region for monitoring the dark current of the light converting means.

* * * * *